(12) United States Patent
Yamagata et al.

(10) Patent No.: US 6,284,552 B1
(45) Date of Patent: Sep. 4, 2001

(54) METHOD AND APPARATUS FOR EVALUATING SURFACE ROUGHNESS OF AN EPITAXIAL GROWTH LAYER, METHOD AND APPARATUS FOR MEASURING REFLECTANCE OF AN EPITAXIAL GROWTH LAYER, AND MANUFACTURING METHOD OF SEMICONDUCTOR DEVICE

(75) Inventors: Hideo Yamagata; Takashi Noguchi; Satoshi Hashidume, all of Kanagawa (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 09/190,461

(22) Filed: Nov. 13, 1998

(30) Foreign Application Priority Data

Nov. 14, 1997 (JP) ................................. P09-313330

(51) Int. Cl.$^7$ .................................................. H01L 21/66
(52) U.S. Cl. .................. 438/14; 438/15; 438/16; 438/29; 438/964
(58) Field of Search .................... 438/15, 29, 16, 438/14, 964

(56) References Cited

U.S. PATENT DOCUMENTS 5,420,796 * 5/1995 Weling et al. ...................... 364/468
5,552,327 * 9/1996 Bachmann et al. ..................... 437/8
5,825,498 * 10/1998 Thakur et al. ....................... 356/394

* cited by examiner

Primary Examiner—John F. Niebling
Assistant Examiner—Olivia T Luk
(74) Attorney, Agent, or Firm—Sonnenschein, Nath & Rosenthal

(57) ABSTRACT

Correlation formulae having predetermined forms (i.e., straight lines representing relationships between the surface roughness of the reflectance) are determined in advance between measurement values of the ultraviolet reflectance of the surfaces of respective sample epitaxial growth layers obtained by using an ultraviolet spectrophotometer at a wavelength of 200 nm and measured values of the surface roughness of the same samples by using an atomic force microscope. The surface roughness of an ensuing measurement object is determined by measuring only its ultraviolet reflectance and substituting a resulting measurement value into the correlation formulae.

16 Claims, 11 Drawing Sheets

FIG.1A
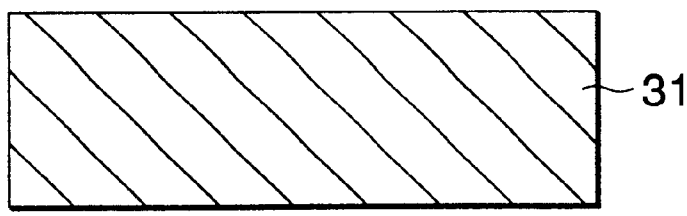
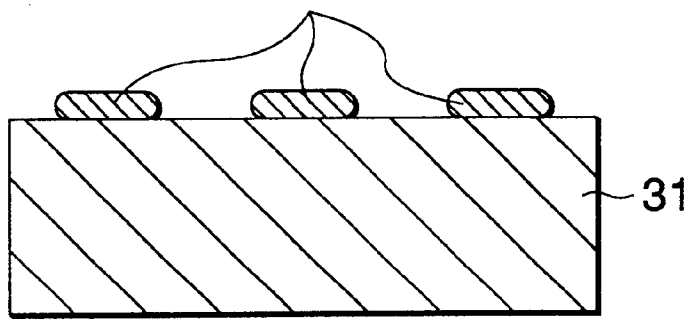
FIG.1B
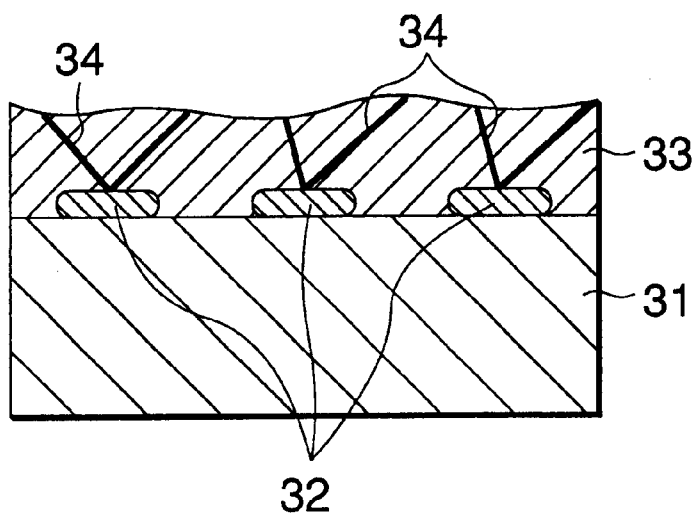
FIG.1C

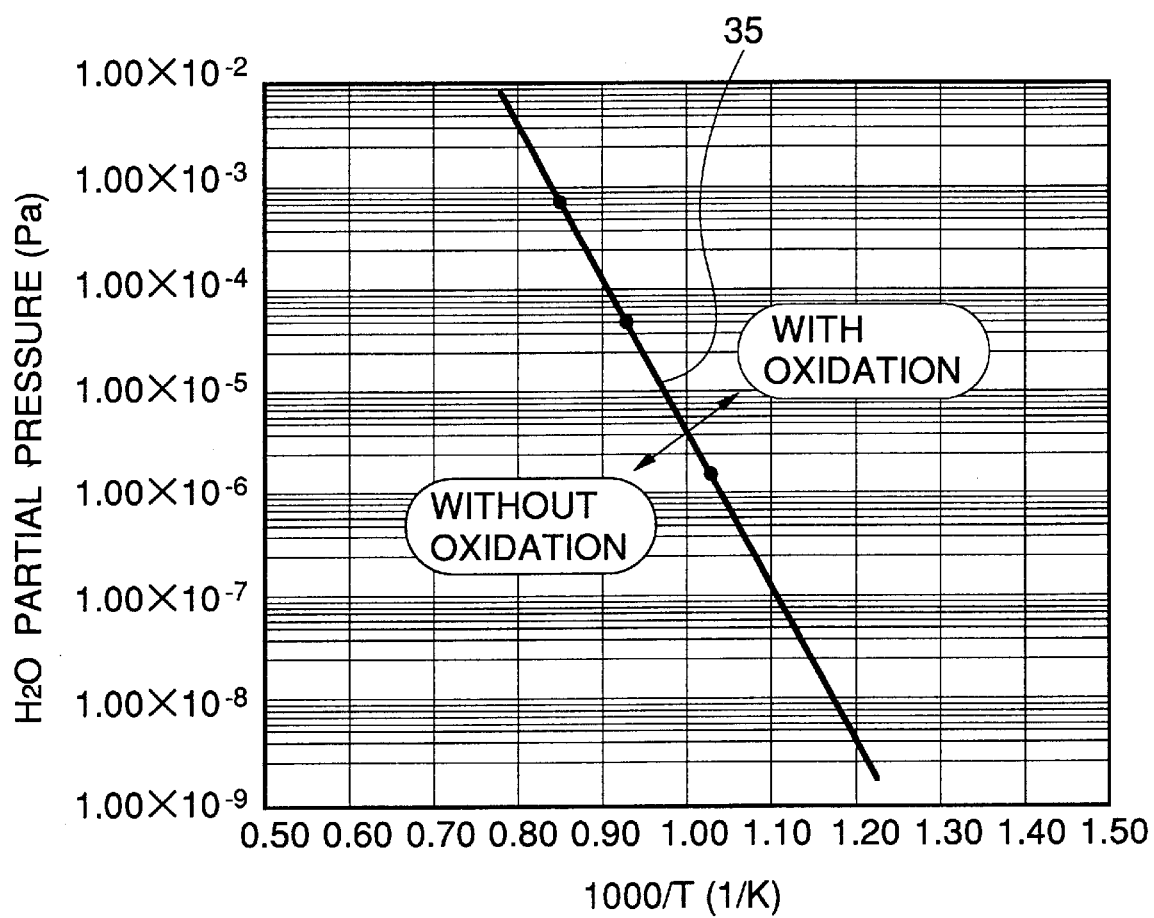

$y = -0.33361 \times R + 29.645$ $y = -3.0819 \times R + 275.49$

US 6,284,552 B1

METHOD AND APPARATUS FOR EVALUATING SURFACE ROUGHNESS OF AN EPITAXIAL GROWTH LAYER, METHOD AND APPARATUS FOR MEASURING REFLECTANCE OF AN EPITAXIAL GROWTH LAYER, AND MANUFACTURING METHOD OF SEMICONDUCTOR DEVICE

BACKGROUND OF THE INVENTION

1. Field of the Invention

The present invention relates to a method and apparatus for evaluating the surface roughness of an epitaxial growth layer, a method and apparatus for measuring the reflectance of an epitaxial growth layer, and a manufacturing method of a semiconductor device which are applicable to, for instance, a case where a base layer of a bipolar transistor that is required to operate at high speed is epitaxially grown.

2. Description of the Related Art

To increase the operation speed of bipolar transistors used in ICs, it is indispensable to form a thin, high-concentration base layer. However, in the conventional ion implantation technology, it is difficult to realize a base width of 40 nm or less because of channeling of an implantation impurity.

In recent years, a method of forming a base layer by using an epitaxial technique which is free of channeling has been studied extensively as one approach for solving the above problem. On the other hand, also in MOSFETs (metal-oxide-semiconductor field-effect transistors), the formation of epitaxial wafers and the selective epitaxial growth of source and drain portions that are advantageous in realizing a short channel have been studied with great expectations.

In the conventional, common silicon epitaxial growth, film formation is performed at as high a temperature as 1,000° C.–1,200° C. in an abundant high-purity hydrogen atmosphere. Therefore, the crystallinity of a resulting silicon epitaxial layer is rarely lowered unless there occurs a damaged layer on the substrate surface for silicon epitaxial growth or contamination of a heavy metal or the like. Further, a resulting silicon epitaxial layer has a flat crystal surface with very low surface roughness.

However, in the above-described case of forming a base layer of a bipolar transistor by epitaxial growth, it is necessary to obtain a steep impurity profile. To this end, the heat treatment temperature should be set as low as possible; silicon epitaxial growth is performed at as low a temperature as 550° C.–900° C.

To perform silicon growth at such a low temperature, film formation should be performed in an atmosphere having a very high level of cleanliness. In particular, epitaxial growth capable of providing good crystallinity cannot be performed unless partial pressures of water and oxygen inside a film forming apparatus are managed so as to be kept sufficiently low. These points are also applicable to the formation of epitaxial wafers and the selective epitaxial growth of source and drain portions for MOSFETs.

The reason why low-temperature silicon epitaxial growth should be performed in a high-cleanliness atmosphere as mentioned above will be described below with reference to FIGS. 1A–1C. Figs. 1A–1C are schematic sectional views of the main part showing a process of causing epitaxial growth on a silicon substrate 31.

When silicon epitaxial growth is performed at a low temperature, even if, for example, a clean surface is produced by a dilute hydrofluoric acid treatment or the like before the silicon substrate 31 is placed in an epitaxial growth apparatus, oxide films 32 are formed on the substrate 31 before occurrence of epitaxial growth or island-like oxide films 32 are formed in the midst of epitaxial growth as shown in FIG. 1B if the partial pressure of water or oxygen inside the apparatus is high. In such a case, stacking faults 34 tend to occur inside an epitaxial growth layer 33 as shown in FIG. 1C because silicon crystal growth is impaired. If the stacking faults 34 occur, the roughness of the surface of the epitaxial growth layer 33 (surface roughness) becomes high and its surface flatness is lowered.

G. Ghidini and F. W. Smith reported a relationship among the possibility of proper epitaxial growth, the growth temperature, and the partial pressure of water in an atmosphere (J. Electrochem. Soc., Vol. 131, p. 2924, 1984). FIG. 2 shows the above relationship that is described in this paper.

As indicated by an epitaxial growth possibility boundary straight line 35, FIG. 2 shows a tendency that oxidation is prone to occur and the surface roughness becomes high (a single crystal is not grown) unless film formation is performed at a water partial pressure that is lower than determined by the line 35 at a preset film forming temperature (horizontal axis). FIG. 2 also shows that oxidation is prone to occur unless the water partial pressure is set lower as the silicon epitaxial growth is performed at a lower temperature. Therefore, in the low-temperature silicon epitaxial growth, it is important to evaluate the crystallinity of an epitaxial growth layer by measuring its surface flatness (i.e., the degree of oxidation) and to feed back a result of the evaluation to the process conditions for the formation of the epitaxial growth layer.

As described above, the surface of a resulting silicon epitaxial layer is roughened if large defect layers exist inside the silicon epitaxial growth layer. The simplest method for evaluating such roughness is visual inspection with a light-gathering lamp in a darkroom. However, since this is based on sensory perception, it cannot evaluate roughness quantitatively.

Therefore, roughness evaluation is now commonly performed by using an atomic force microscope (AFM) which can detect asperity of an atomic level. However, the surface roughness measurement with an atomic force microscope is influenced by external vibration or noise. Therefore, it is necessary to provide an antivibration, soundproof structure at a location where a measuring apparatus is to be installed, which increasing the installation cost. Further, a measurement requires a high degree of skill and know-how of measurement techniques. There are additional drawbacks such as a long measurement time.

SUMMARY OF THE INVENTION

An object of the present invention is to provide a method and apparatus for evaluating the surface roughness of an epitaxial growth layer, a method and apparatus form easuring the reflectance of an epitaxial growth layer, and a manufacturing method of a semiconductor device which eliminates the loss of time in development or manufacture of an epitaxial thin film by evaluating the surface roughness of an epitaxial growth layer simply and conveniently, and which contributes to manufacture of high-quality products by quickly recognizing occurrence of oxygen mixing (that obstructs growth of a single crystal) and the number of oxygen-containing defects and feeding back such information to a semiconductor manufacturing apparatus, epitaxial growth layer forming conditions, or the like.

As a result of concentrated studies to attain the above object, the present inventors have found an effective solution and completed the invention.

The invention provides a method for evaluating surface roughness of an epitaxial growth layer formed on a substrate (hereinafter referred to as the evaluation method of the invention), comprising the steps of measuring reflectance of epitaxial growth layers by applying shorter-wavelength ultraviolet light to surfaces of the respective epitaxial growth layers; and determining a correlation between measurement values of the reflectance and surface roughness of the epitaxial growth layers.

In the evaluation method of the invention, a correlation between the reflectance and the surface roughness of epitaxial growth layers is determined and the surface roughness of an ensuing epitaxial growth layer is evaluated based on the thus-determined correlation. Therefore, it is not necessary to perform a surface roughness measurement on each ensuing epitaxial growth layer and hence the surface roughness can be evaluated simply and conveniently. As a result, the loss of time in development or manufacture of, for instance, a silicon epitaxial thin film can be reduced, and a manufacturing process, epitaxial growth layer forming conditions, or the like can be improved by quickly recognizing occurrence of oxygen mixing (that obstructs growth of a single crystal) and the number of resulting defects and feeding back such information.

The invention also provides an apparatus for evaluating surface roughness of an epitaxial growth layer formed on a substrate (hereinafter referred to as the evaluation apparatus of the invention), comprising reflectance measuring means for measuring reflectance of epitaxial growth layers by applying shorter-wavelength ultraviolet light to surfaces of the respective epitaxial growth layers; and evaluating means for evaluating the surface roughness by determining a correlation between measurement values of the reflectance and surface roughness of the epitaxial growth layers.

Since the evaluation apparatus of the invention is based on the above evaluation method, it can evaluate the surface roughness of an epitaxial growth layer easily and conveniently.

According to another aspect of the invention, there is provided a method for measuring reflectance of an epitaxial growth layer formed on a substrate to evaluate surface roughness of the epitaxial growth layer (hereinafter referred to as the measuring method of the invention), comprising the step of measuring specular reflectance of the epitaxial growth layer with an ultraviolet spectrophotometer by applying shorter-wavelength ultraviolet light to a surface of the epitaxial growth layer at an incident angle of about 90°.

Since ultraviolet light is applied to the surface of an epitaxial growth layer at an incident angle of about 90°, the measuring method of the invention provides a proper reflectance value. Therefore, by inputting the measured reflectance value to, for instance, the above evaluation apparatus, the surface roughness of the epitaxial growth layer can easily be determined (quantified) based on the predetermined correlation without the need for performing a surface roughness measurement.

The invention also provides an apparatus for measuring reflectance of an epitaxial growth layer formed on a substrate to evaluate surface roughness of the epitaxial growth layer (hereinafter referred to as the measuring apparatus of the invention), comprising reflectance measuring means for measuring specular reflectance of the epitaxial growth layer with an ultraviolet spectrophotometer by applying shorter-wavelength ultraviolet light to a surface of the epitaxial growth layer at an incident angle of about 90°.

Since the measuring apparatus of the invention is based on the above measuring method, it can easily evaluate the surface roughness of an epitaxial growth layer.

According to a further aspect of the invention, there is provided a manufacturing method of a semiconductor device (hereinafter referred to as the manufacturing method of the invention) comprising the step of forming an epitaxial growth layer on a semiconductor substrate, further comprising the steps of measuring reflectance of epitaxial growth layers by applying shorter-wavelength ultraviolet light to surfaces of the respective epitaxial growth layers; and determining a correlation between measurement values of the reflectance and surface roughness of the epitaxial growth layers.

By using the evaluation method of the invention, the manufacturing method of the invention makes it possible to easily evaluate the surface roughness of an epitaxial growth layer formed on a semiconductor substrate. The manufacturing method of the invention contributes to manufacture of high-quality products by improving the film forming conditions by, for instance, feeding back an evaluation result of the surface roughness to the step of forming an epitaxial growth layer.

In the above evaluation method and apparatus, measuring method and apparatus, and manufacturing method of the invention, it is desirable to measure the specular reflectance of an epitaxial growth layer by using an ultraviolet spectrophotometer with an incident angle of the ultraviolet light with respect to the surfaces of the respective epitaxial growth layers set at about 90°.

In this case, it is desirable that the ultraviolet light have a wavelength in a range of 190 to 210 nm (more desirably 200 nm). Ultraviolet light whose wavelength is out of the above range can still be used if it can provide a large reflectance value and allows determination of a correlation between the reflectance and the surface roughness.

In the evaluation apparatus of the invention, it is desirable that the evaluating means comprise computing means having a computer that is connected to the reflectance measuring means, for determining the correlation, and output means for outputting a computation result of the computing means.

It is desirable that surface roughness of a second epitaxial growth layer be quantified by using a measurement value of ultraviolet specular reflectance of the second epitaxial growth layer by measuring surface roughness of first epitaxial growth layers by using an atomic force microscope and determining a correlation between measurement values of the surface roughness and measurement values of ultraviolet specular reflectance of the first epitaxial growth layers.

In this case, it is desirable that the computing means determine a correlation formula of the correlation, and then determine the surface roughness of the second epitaxial growth layer by substituting the measurement value of the specular reflectance into the correlation formula.

In a case where the substrate is a silicon substrate and the epitaxial growth layer is a silicon epitaxial growth layer, it is desirable that correlations between measurement values of root-mean-square roughness RMS and a maximum height Rmax of surfaces of the first epitaxial growth layers obtained by using the atomic force microscope and the measurement values of the ultraviolet specular reflectance R of the first epitaxial growth layers be formulated as correlation formulae.

$$RMS = -a \times R + b$$

$$Rmax = -c \times R + d \qquad (A)$$

where a, b, c, and d are constants.

In the manufacturing method of the invention, it is desirable to evaluate surface roughness of an epitaxial growth layer, and to control conditions (for instance, temperature) for forming an ensuing epitaxial growth layer based on an evaluation result of the surface roughness.

This makes it possible to form a silicon epitaxial growth layer as a base layer that is thin, has a high concentration, and is superior in surface flatness (i.e., oxidation is suppressed) on a silicon substrate as a semiconductor substrate at a selected low temperature. As a result, it becomes possible to manufacture a vertical bipolar transistor properly.

Although the use of an atomic force microscope is suitable for the above surface roughness measurement, a scanning tunnel microscope or the like may also be used for this purpose.

BRIEF DESCRIPTION OF THE DRAWINGS

FIGS. 1A–1C are schematic sectional views showing a process of epitaxial growth;

FIG. 2 is a graph showing occurrence of film oxidation in connection with a relationship between the temperature and the water partial pressure (oxygen partial pressure) during epitaxial growth;

DETAILED DESCRIPTION OF THE PREFERRED EMBODIMENTS

An evaluation method and apparatus and a measuring method and apparatus according to the present invention will be hereinafter described in detail with reference to the accompanying drawings.

The evaluation method is such that the surface roughness of an epitaxial layer is quantified by measuring the ultraviolet reflectance of the surface of an epitaxial growth layer by applying ultraviolet light having a wavelength of 190–210 nm, preferably 200 nm, at an incident angle of about 90°, and then determining correlations between resulting measurement values and root-mean-square roughness (RMS) and a maximum height (Rmax) that are determined by using an atomic force microscope. In the invention, RMS and Rmax are ones that comply with the JIS surface roughness standard (BO601).

Specifically, first, a plurality of samples on which epitaxial growth layers are formed respectively under different film forming conditions are prepared. Correlations as mentioned above are determined for those samples; that is, surface roughness vs. reflectance correlation formulae are determined by a computing section such as a computer that is connected to a reflectance measuring apparatus (described later). Thereafter, for a second group of epitaxial growth layers, only the ultraviolet reflectance is measured and a resulting measurement value is automatically input to the computing section and subjected to computation therein, whereby a surface roughness value of a subject of measurement is output as a quantified value.

Figure 3:
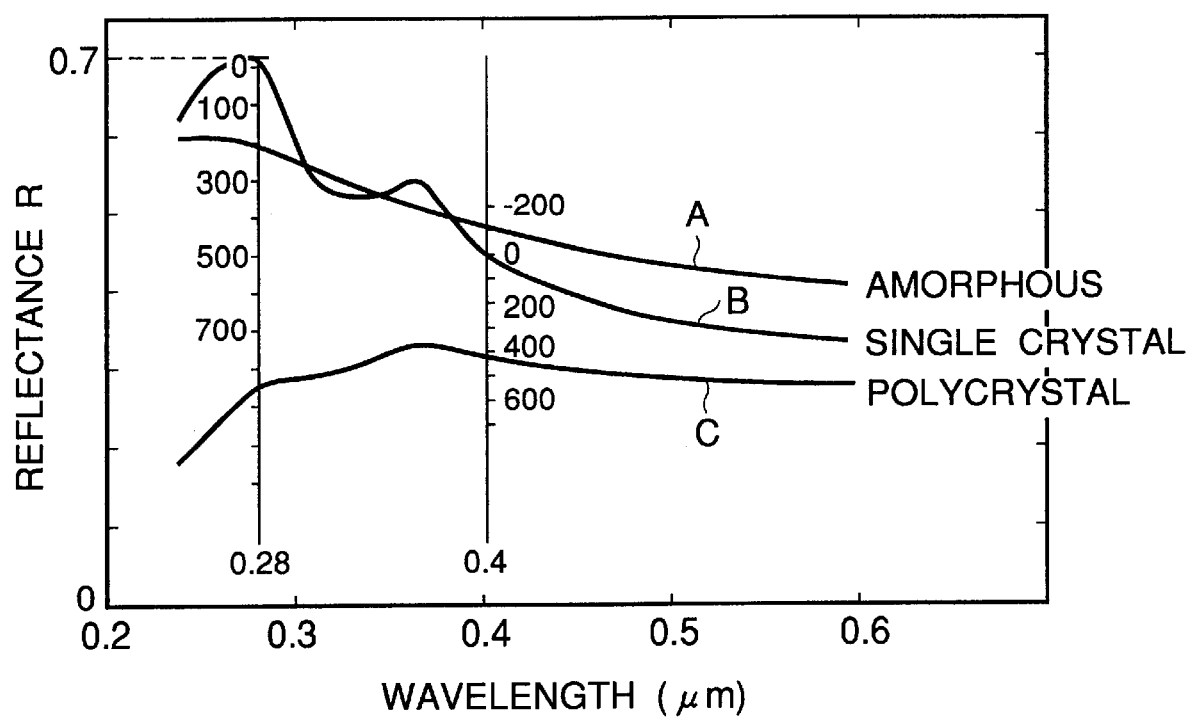
FIG. 3 is a graph showing reflectance vs. wavelength relationships of amorphous silicon, single crystal silicon, and polysilicon.

As shown in FIG. 3, a relationship between the wavelength of ultraviolet light and the reflectance has been reported by G. Harbecke et al. (RCA Review, Vol. 144, 1983) as reflection spectra of light in an ultraviolet range, that is, a curve B of single crystal silicon, a curve C of polysilicon, and a curve A of amorphous silicon.

The reflection spectrum B of single crystal silicon at room temperature in the ultraviolet range has the maximum peak at a wavelength 280 nm (about 4.4 eV) On the other hand, the reflection spectrum A of amorphous silicon in the ultraviolet range does not have a peak. The peak at 280 nm (about 4.4 eV) means formation of a single crystal structure.

In polycrystal silicon, crystal grains have various sizes and shapes. The size of crystal grains in a surface portion of a thin film, that is, the state of crystallization, can be determined from a peak shape of a reflection spectrum in an ultraviolet range. That is, the crystallinity (degree of crystallization) of polysilicon can be determined by calculating the area or height of an ultraviolet reflection peak at 270–280 nm by using, as a base line, a common tangential line connecting a minimum point at about 240 nm and a minimum point at about 340 nm. The calculated area or height is expressed as a ratio that is 100% in the case of single crystal and 0% in the case of amorphous silicon.

Under certain limited conditions, it is possible to effect quantification by correlating the above value with a grain size of polysilicon that is determined by a transmission electron microscope (TEM) analysis.

It is known that there is the following relationship among the reflectance R measured through the above-described ultraviolet light reflection, the surface roughness σ, and the wavelength λ.

$$R \propto \exp(-4\pi\sigma/\lambda) \quad (1)$$

It is understood from Equation (1) that the reflectance measured through ultraviolet light reflection varies so as to be greatly influenced by the surface roughness in a shorter wavelength range. In other words, information about a surface portion can be obtained in a shorter wavelength side (K. L. Chiang et al., J. Electrochem. Soc., Vol. 126, p. 2267, 1979).

Returning to the invention, the inventors have experimentally confirmed that Equation (1) also holds for a silicon epitaxial growth layer on a silicon substrate. Further, the inventors have first found experimentally that there is a correlation between the reflectance R by an ultraviolet reflectance measurement and the surface roughness value determined by using an atomic force microscope (AFM). The inventors have also found that the physical mechanism relating to this correlation is represented by stacking faults due to oxygen mixing during growth of an epitaxial layer. This will be described later in detail.

Figure 4:
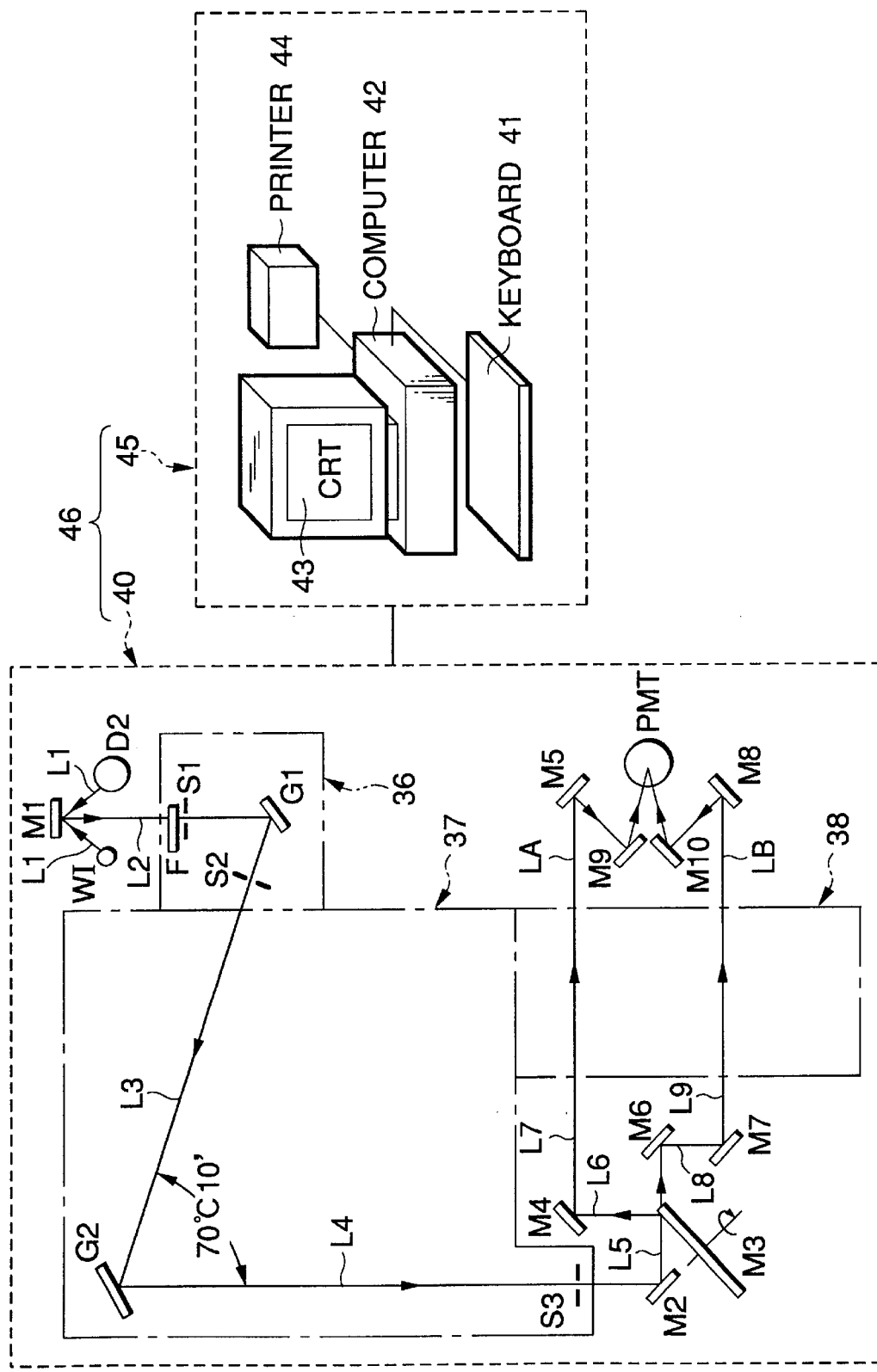
FIG. 4 is a schematic diagram showing an apparatus for evaluating the surface roughness of an epitaxial growth layer according to the present invention.

FIG. 4 is a schematic diagram showing an evaluation apparatus according to the above-described evaluation method which is composed of a reflectance measuring section 40 that is an ultraviolet spectrophotometer and a computing section 45.

The ultraviolet spectrophotometer 40 applies ultraviolet light to a subject of measurement by using a spectroscope while switching between two kinds of lamps, that is, a deuterium lamp D2 and an iodine-tungsten lamp W1.

Ultraviolet light L1 that is emitted from the deuterium lamp D2 or the iodine-tungsten lamp W1 is reflected by a light source light-gathering mirror M1 to become reflection light L2, which enters a first spectroscope 36. A filter F allows input of only part of the incident light L2 having a wavelength, and ultraviolet light having the same polarization component passes through a slit S1 and is then reflected by a toroidal diffraction grating G1. Ultraviolet light having the same polarization component of resulting reflection light L3 passes through a slit S2 and enters a second spectroscope 37. The incident light L3 is reflected by a variable-pitch aberration-correcting diffraction grating G2 to become reflection light L4. A slit S3 allows ultraviolet light having the same polarization component of the reflection light L4 to be output from the second spectroscope 37.

The ultraviolet light L4 that has been output from the second spectroscope 37 is reflected by a cylindrical lens M2 to become reflection light L5, which takes one of an optical path along which it enters a sample chamber 38 as reference light L7 via a rotary mirror M3 and a plane mirror M4 and an optical path along which it enters the sample chamber 38 as measurement light L9 via the rotary mirror M3 and plane mirrors M6 and M7. That is, when passing through a through-hole (not shown) that is formed in the rotary mirror in the circumferential direction, the ultraviolet light L5 goes straight to form an optical path toward the plane mirror M6.

FIGS. 5A–5B and 6A–6B are schematic enlarged views showing the arrangement of an optical system and variations of the optical axis of ultraviolet light in the sample chamber 38.

Figure 5A:
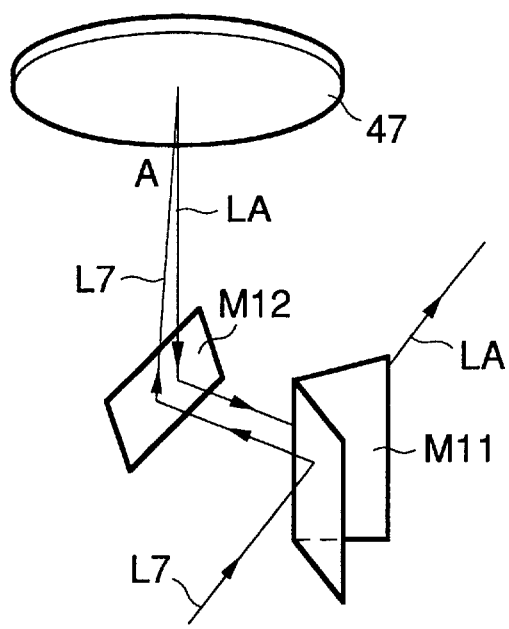
FIGS. 5A is a schematic perspective view showing an optical path of reference light in a sample chamber of the evaluation apparatus of FIG. 4.

A reference (aluminum mirror) 47 is provided in an upper portion of the sample chamber 38. As shown in FIG. 5A, the ultraviolet light L7 entering the sample chamber 38 (see FIG. 4) is reflected by one surface of a double-face mirror M11 and a plane mirror M12 and reaches the reference 47 at an incident angle of about 90°. The ultraviolet light L7 is reflected by the reference 47 to become reference reflection light LA, which reflected by the plane mirror M12 and the other surface of the double-face mirror M11, and is then output from the sample chamber 38.

Figure 5B:
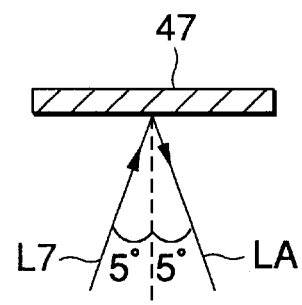
FIG. 5B is an enlarged sectional view of part A of FIG. 5A.

Since the reflection by the reference 47 occurs symmetrically with respect to the normal (i.e., the reflection angle is equal to the incident light) as shown in FIG. 5B, the incident light L7 and the reflection light LA form an angle of about 10° with the normal located at the center. However, a reflectance value close to 100% can be obtained.

Figure 6A:
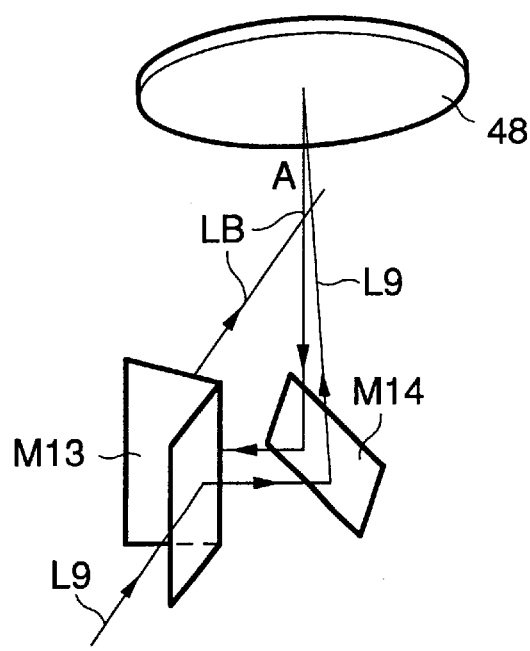
FIGS. 6A is a schematic perspective view showing an optical path of measurement light in the sample chamber of the evaluation apparatus of FIG. 4.
Figure 6B:
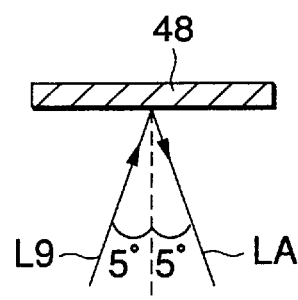
FIG. 6B is an enlarged sectional view of part A of FIG. 6A.

A measurement object 48 is provided in the vicinity of a central portion of the sample chamber 38. As shown in FIG. 6A, the ultraviolet light L9 entering the sample chamber 38 (see FIG. 4) is reflected by one surface of a double-face mirror M13 and a plane mirror M14 and impinges on the surface of the measurement object (silicon epitaxial growth layer) 48 at an incident angle of about 90°. Resulting reflection light LB is reflected by the plane mirror M14 and the other surface of the double-face mirror M13, and is then output from the sample chamber 38 as specular reflection light of the measurement object 48.

Since the reflection by the measurement object 48 occurs so that the incident light L9 and the reflection light LB form an angle of about 10° with the normal located at the center (the incident angle is about 90°, i.e., 85°). Therefore, while the reference 47 provides a reflectance value 100% as described above in connection with FIGS. 5A and 5B, a specular reflectance value of the measurement object 48 is obtained by using the same ultraviolet light.

Returning to FIG. 4, the reference reflection light LA that is output from the sample chamber (see FIGS. 5A and 5B) is reflected by a toroidal mirror M5 and a plane mirror M9 and then enters a photomultiplier tube PMT. On the other hand, the measurement reflection light LB that is output from the sample chamber 38 (see FIGS. 6A and 6B) is reflected by a toroidal mirror M8 and a plane mirror M10 and then enters the photomultiplier tube PMT.

As shown in FIG. 4, the reflectance measuring section 40 is connected to the computing section 45. After the measurement object 48 is placed in the sample chamber 38, a reflectance measurement on the surface of the measurement object 48 can be completed automatically only by inputting a measurement start signal by manipulating a keyboard 41 in the computing section 45.

Reflectance measurement values of measurement objects are input to a computer 42, and surface roughness measurement values of the measurement objects obtained by using an atomic force microscope (described later) are also input to the computing section 45. Correlation formulae (A) of the two kinds of measurement values are automatically determined and displayed on a display section 43 of the computing section 45 together with the measurement values.

Figure 7:
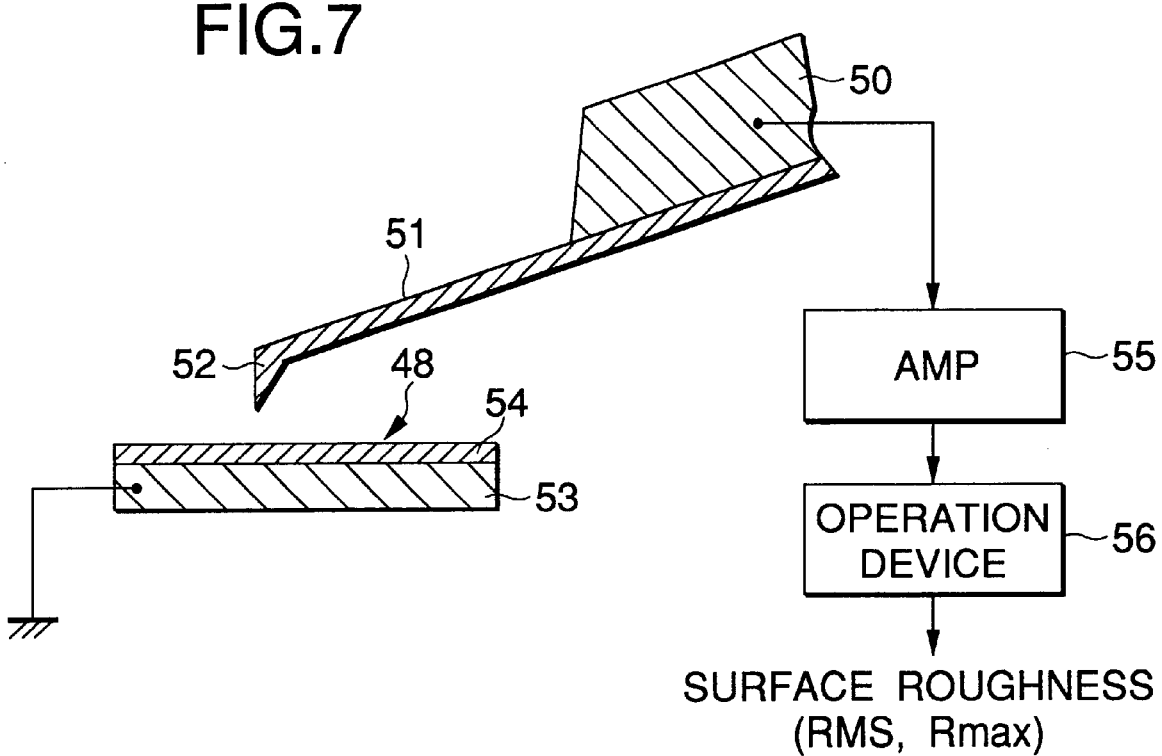
FIG. 7 is a schematic sectional view showing part of an atomic force microscope.

FIG. 7 is a schematic view showing part of the main part of an atomic force microscope, that is, a measurement object, a cantilever, etc.

The atomic force microscope is composed of an electrode 50, a cantilever 51, and a probe 52 that is attached to the cantilever 51 that is a thin leaf spring mounted on the electrode 50. A measurement object 48 is mounted levelly on a substrate stage (not shown). The probe 52, which was formed by microprocessing at the tip of the cantilever 51, is arranged vertically with a predetermined gap interposed between the probe 52 and the measurement object 48 (i.e., an epitaxial layer 54).

As shown in FIG. 7, a substrate 53 is grounded and the cantilever 51 is connected to the electrode 50. Therefore, a very small variation in the atomic force that occurs between the minute probe 52 and the measurement object 48 when the substrate 53 is scanned with the probe 52 in a state that the probe 52 is brought close to the surface of the measurement object 48 is detected as a bend of the cantilever 51. The variation in the atomic force occurring between the probe 52 and the measurement object 48 is converted into a very small current, which is amplified by an amplifier 55. An amplified signal is subjected to computation by an operation device 56, whereby asperity at each position on the surface of the measurement object 48 is measured as surface roughness (RMS and Rmax).

Figure 8A:
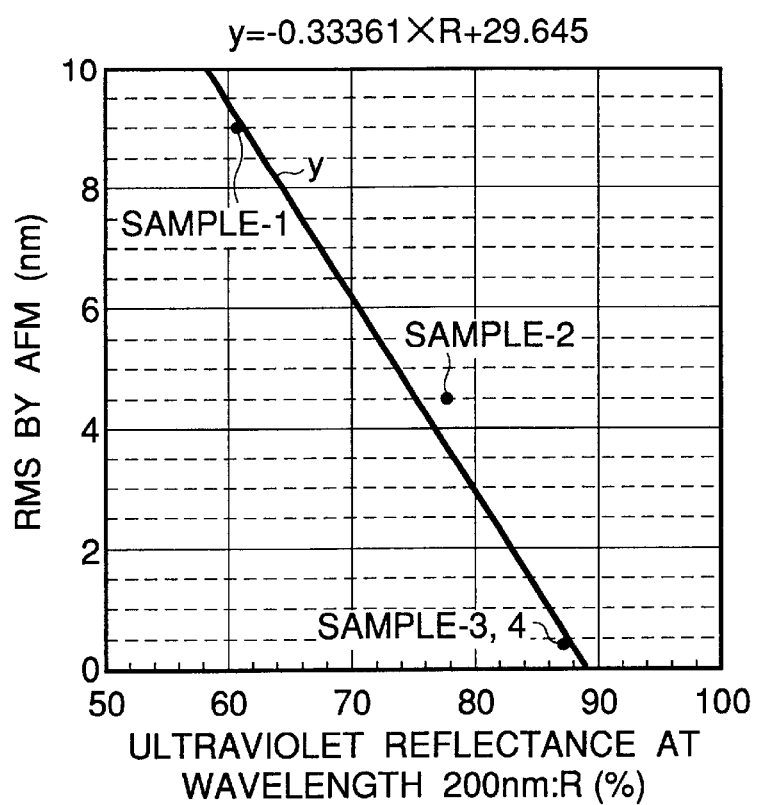
FIGS. 8A and 8B are graphs showing straight lines representing relationships between the surface roughness (root-mean-square roughness RMS and maximum height Rmax) and the reflectance that are obtained in a method for evaluating the surface roughness of an epitaxial growth layer according to the invention.
Figure 8B:
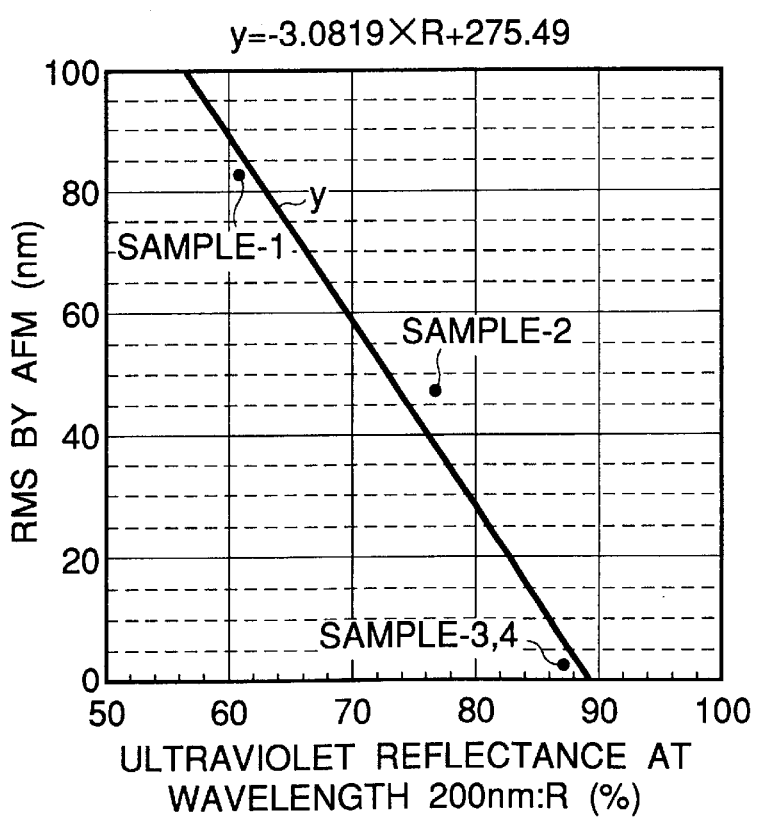

As described above, a plurality of epitaxial growth layers are produced as samples. The specular reflectance of each sample is measured by the previously described measuring apparatus and a measurement value is input to the computing section 45. The surface roughness of each sample is measured by the atomic force microscope and measurement values are also input to the computing section 45. Based on those measurement values, the computing section 45 determines a correlation between the specular reflectance and the surface roughness. In this manner, relationships between the reflectance of ultraviolet light having a wavelength 200 nm and the root-mean-square roughness (RMS) and the maximum height (Rmax) of the sample surfaces can be formulated as first order equations (Equations (A)) as shown in FIGS. 8A and 8B.

The correlation formulae thus determined by measuring the samples are stored in the computing section 45. Therefore, for ensuing measurement objects, the surface roughness of an epitaxial growth layer can be determined automatically by a calculation by inputting, to the computing section 45, a measurement value of the specular reflectance of the surface of the epitaxial growth layer obtained by the previously described measuring apparatus, and causing the computing section 45 to calculate the surface roughness by substituting the measurement value into the correlation formulae. Quantified values of the surface roughness can thus be known; they can be output by the printer 44 or the display section 43 shown in FIG. 4.

Since it is not necessary to perform a surface roughness measurement with the atomic force microscope each time, the above-mentioned drawbacks of the use of an atomic scope microscope, such as a long measurement time, can be lowered and it becomes possible to determine the surface roughness simply and conveniently.

The above method and apparatus for evaluating the surface roughness of an epitaxial growth layer according to the invention are measures for solving the problems that are associated with the requirement of increasing the operation speed of bipolar transistors. Next, with reference to FIGS. 9–16, a description will be made of a manufacturing process of a bipolar transistor capable of operating at high speed as a semiconductor device to which the invention can be applied.

Figure 9:
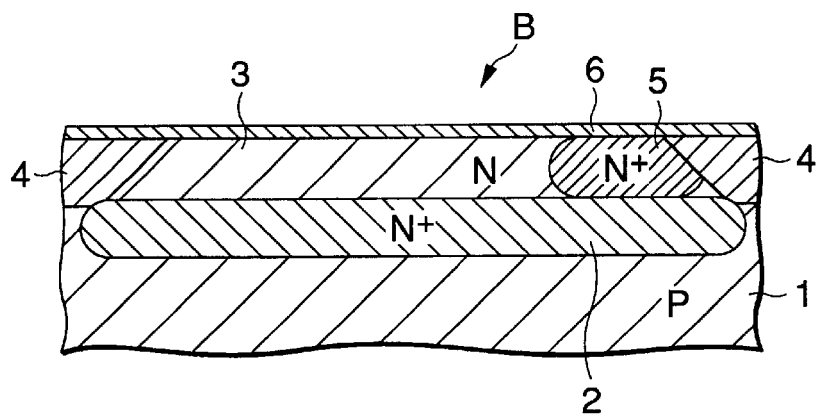
FIGS. 9–16 are schematic sectional views showing a manufacturing process of a semiconductor device.

First, as shown in FIG. 9, after an $n^+$ buried layer 2 is formed in a surface portion of a p-type single crystal silicon semiconductor substrate 1 by, for instance, ion implantation, an n-type epitaxial layer 3 to become collector layer is grown on the entire surface of the silicon substrate 1.

Then, a field oxide film 4 is formed by, for instance, by thermally oxidizing in a selective manner the n-type epitaxial layer 3 that constitutes the substrate surface portion, whereby a device forming region B is formed that is enclosed by the field oxide film 4. Then, a collector pickup $n^+$ layer 5 is formed in the n-type epitaxial layer 3 (i.e., in the device forming region B) by ion implantation, for instance.

Thereafter, a silicon nitride film 6 of about 100 nm in thickness is formed on the entire surface by chemical vapor deposition (CVD), for instance. Instead of the silicon nitride film 6, for example, a laminated film of a silicon nitride film and a relatively thin silicon oxide film (what is called a NO composite film) may be used.

Figure 10:
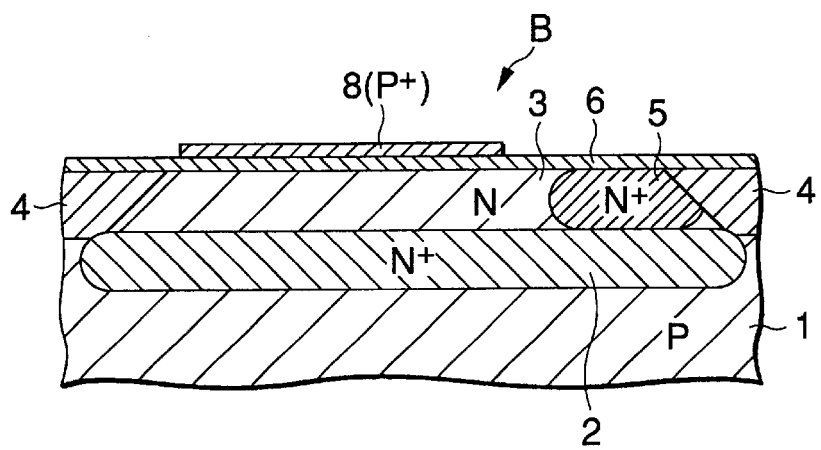

Subsequently, as shown in FIG. 10, a polysilicon film of, for instance, about 200 nm in thickness that is doped with a p-type impurity at a relatively high concentration is formed on the entire surface by CVD, and then patterned by photolithography and dry etching so that a polysilicon film 8 is left in a predetermined region of the device forming region B that includes a region where a base layer of the bipolar transistor will be formed.

The introduction of the p-type impurity into the polysilicon film 8 may be performed either at the time of the CVD or after the film formation by ion implantation. For example, the impurity concentration of the polysilicon film 8 can be set as high as about $1\times10^{20}$ cm$^{-3}$ or more by performing ion implantation of boron (B) after the film formation under conditions that the acceleration energy is about 20 keV and the dose is about $5\times10^{15}$ cm$^{-2}$.

Figure 11:
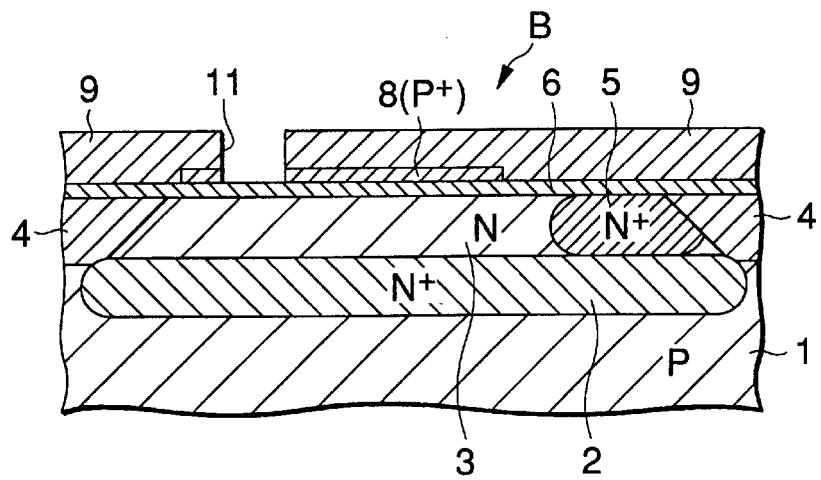

Then, as shown in FIG. 11, a silicon oxide film 9 of, for instance, about 300 nm in thickness is formed on the entire surface by CVD.

Then, a through-hole 11 is formed through the silicon oxide film 9 and the polysilicon film 8 by photolithography and dry etching in a region where a base layer of the bipolar transistor will be formed. In this step, the silicon nitride film 6 serves as an etching stopper when the polysilicon film 8 is etched. Therefore, the through-hole 11 is so formed as to penetrate through only the silicon oxide film 9 and the polysilicon film 8 on the silicon nitride film 6.

Then, the side face of the polysilicon film 8 that is exposed in the through-hole 11 is thermally oxidized, whereby a silicon oxide film 13 of, for instance, 10–30 nm in thickness is formed there.

Figure 12:
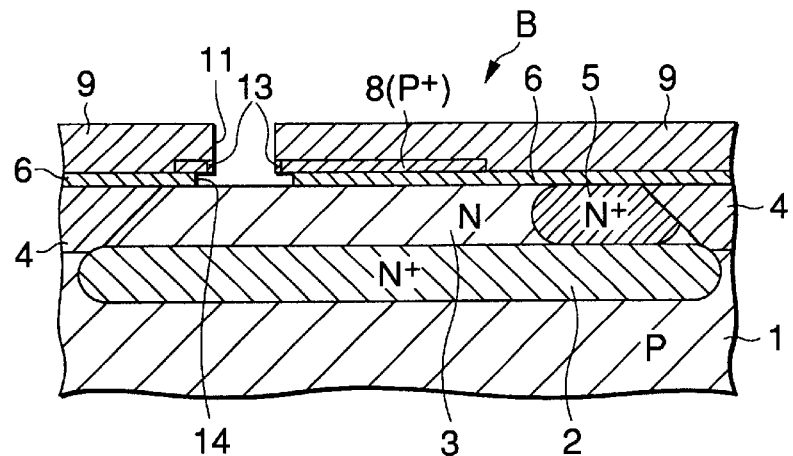

Thereafter, as shown in FIG. 12, the silicon nitride film 6 is wet-etched with, for instance, a heated phosphoric acid solution via the through-hole 11 in the device forming region B, whereby an opening 14 that is wider than the through-hole 11 is formed in the silicon nitride film 6. In this manner, the opening 14 is formed so as to be self-aligned with the through-hole 11 without the need for any masking step.

Figure 13:
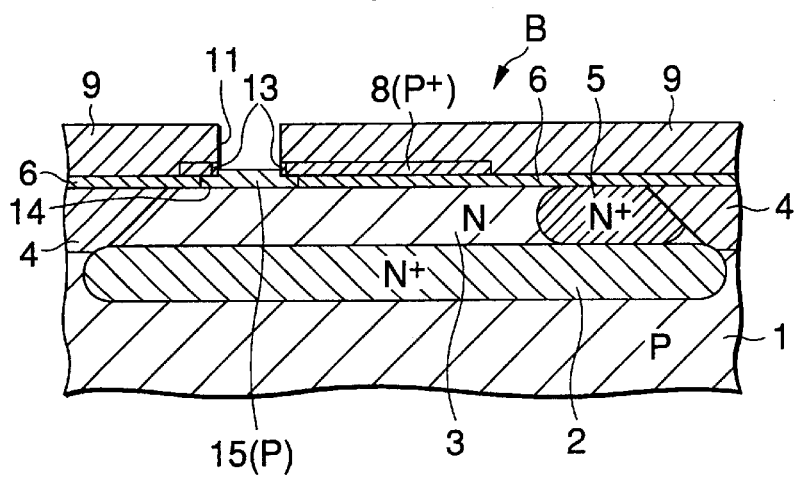

Then, as shown in FIG. 13, a p-type epitaxial base layer 15 is grown on the part of the n-type epitaxial layer 3 that is exposed in the opening 14 by a selective epitaxy technique via the through-hole 11 and the opening 14 in the device forming region B. The above-described evaluation of an epitaxial growth layer is to be performed on this epitaxial base layer 15. In the evaluation method of the invention, it is preferable that measurements be performed by using wafers on which epitaxial growth layers are formed as monitoring samples under the same film forming conditions as the epitaxial base layer 15 is formed.

A p-type silicon epitaxial base layer 15 containing boron (B) can be formed by causing epitaxial growth under conditions of, for instance, 725° C. and 10 Torr by using, for instance, a mixed gas of $H_2$, $SiH_2Cl_2$, HCl, $GeH_4$, and $B_2H_6$. From the viewpoint that the bipolar transistor should operate at high speed, it is preferable that the base layer contains germanium (Ge). Naturally, a p-type epitaxial base layer made of only SiGe can be formed by changing the composition of the above mixed gas.

Since the opening 14 of the silicon nitride film 6 is wider than the through-hole 11 of the polysilicon 8, a crystal grows also from the bottom face of the polysilicon film 8 in the gap that is interposed between the polysilicon film 8 and the n-type epitaxial layer 3 in the opening 14. This provides advantages that the p-type impurity diffuses from the polysilicon film 8 into the epitaxial base layer 15 and that the entire epitaxial base layer is given better crystallinity.

Further, the silicon oxide film 13 that is formed on the side face of the polysilicon film 8 and constitutes part of the through-hole 11 prevents epitaxial growth from the side face of the polysilicon film 8. Therefore, the epitaxial base layer 15 grows substantially only from below and hence is given good crystallinity and shape in its entirety. It is noted that the side insulating film of the polysilicon film is not always necessary.

Figure 14:
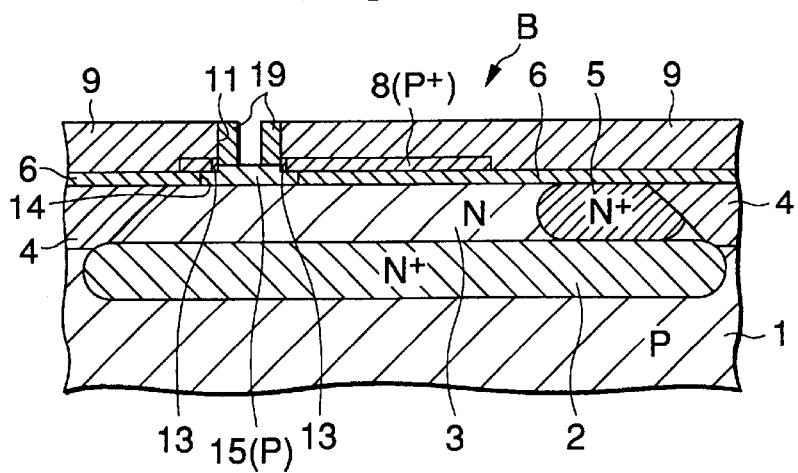

Thereafter, as shown in FIG. 14, a silicon oxide film is formed by CVD on the entire surface including the inside surface of the through-hole 11, and then anisotropically etched so that a sidewall oxide film 19 is left only inside the through-hole 11. After the formation of the silicon oxide film 19, a heat treatment may be performed so that the surface of the p-type epitaxial base layer 15 in the device forming region B is oxidized via the silicon oxide film 19. This increases the breakdown voltage of a resulting high-speed bipolar transistor in the device forming region B, as well as improves the film quality of the silicon oxide film 19 that has been formed by CVD.

Figure 15:
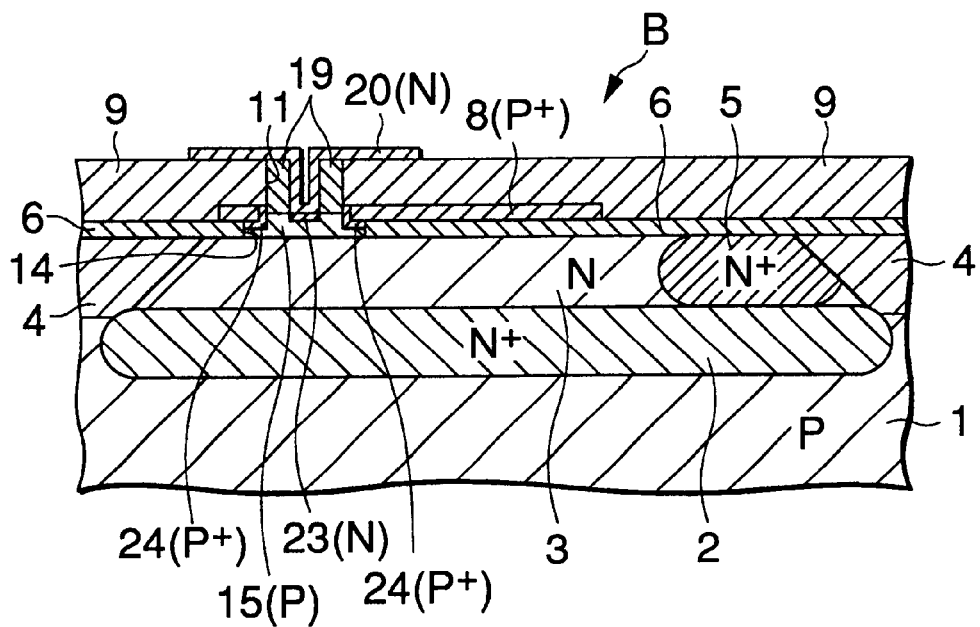

Subsequently, as shown in FIG. 15, an n-type polysilicon film is formed by CVD on the entire surface of the silicon oxide film 9 including the sidewall oxide film 19 in the through-hole 11 and then patterned by photolithography and etching, whereby a polysilicon film emitter pickup electrode 20 is formed in a predetermined region including a region in the through-hole 11. The introduction of the n-type impurity into the polysilicon film 20 may be performed either at the time of the formation of the polysilicon film 20 or after the formation of the polysilicon film 20 by ion implantation.

Thereafter, a heat treatment is performed so that the n-type impurity diffuses from the emitter pickup electrode 20 into a surface region of the underlying portion of the p-type epitaxial base layer 15 and an n-type emitter region 23 is thereby formed in the surface region of the p-type epitaxial base layer, and that the p-type impurity is diffused from the polysilicon film 8 as a base pickup electrode into a surface region of the underlying portion of the p-type epitaxial base layer 15 and a higher-concentration $p^+$ external base region 24 (serving for reduction of the base contact resistance) is thereby formed in the surface region of the p-type epitaxial base layer 15.

Figure 16:
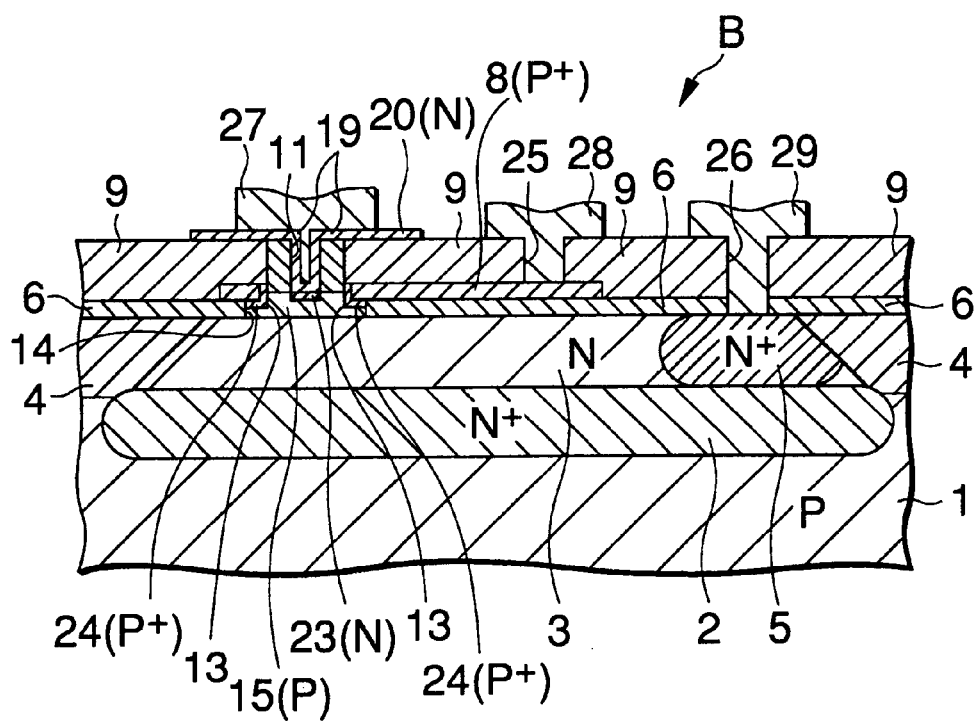

Then, as shown in FIG. 16, photolithography and etching are performed so that a through-hole 25 is formed at a predetermined position through the silicon oxide film 9 so as to reach the polysilicon film 8 as the base pickup electrode, and that a through-hole 26 is formed at a predetermined position through the silicon oxide film 9 and the silicon nitride film 6 so as to reach the collector pickup $n^+$ layer 5.

Thereafter, a metal film of aluminum (Al) or an aluminum alloy is formed on the entire surface so as to fill in the through-holes 25 and 26 and then patterned by photolithography and etching, to thereby form an emitter electrode 27 on the emitter pickup electrode 20, a base electrode 28 that is electrically connected to the polysilicon film 8 through the through-hole 25, and a collector electrode 29 that is electrically connected to the $n^+$ layer 5 through the through-hole 26, as shown in FIG. 16.

As a result of the execution of the above steps, a high-speed vertical npn bipolar transistor is formed on the silicon semiconductor substrate 1 in such a manner that the base layer 15 is formed by the epitaxy technique in the device forming region B.

As for the above semiconductor device, samples for measurement and evaluation are merely ones for determining a correlation that are formed on, for instance, dummy wafers, and will not be used as products after a measurement.

The evaluation method of the invention is used in the manufacturing method of FIGS. 9–16. That is, surface roughness measurement values and reflectance measurement values are obtained by using the atomic force microscope and the ultraviolet spectrophotometer from monitoring wafers that are manufactured under the same film forming conditions as the epitaxial growth layer 15 as the base layer is formed on a semiconductor substrate, and the correlation formulae (A) are determined based on those measurement values. Surface roughness values are calculated based on ultraviolet reflectance measurement values of base layers on another wafer are calculated by using the correlation formulae (A). Based on the thus-calculated surface roughness values, feedback is made to the conditions such as the temperature of the epitaxial growth to improve the conditions. In this manner, the invention contributes to manufacture of high-quality products.

For example, as seen from FIG. 2, a base layer that is free of oxidation, has a high concentration and a small thickness, and has good film quality can be epitaxially grown at a low temperature by properly adjusting the water partial pressure in an apparatus capable of suppressing oxidation through a temperature control.

EXAMPLE

The invention will be hereinafter described in more detail by using an Example.

First, four samples were prepared by low-temperature epitaxial growth in such a manner that manufacturing conditions such as the water and oxygen partial pressures of a film forming atmosphere and the film forming temperature are different from one another as shown in Table 1.

The samples were prepared in an ultrahigh vacuum CVD apparatus by using monosilane ($SiH_4$) as a material gas for epitaxial growth. Referring to Table 1, preprocess-1 was executed before input to the epitaxial growth apparatus and preprocess-2 was executed in the epitaxial growth apparatus.

TABLE 1

| Sample No. | 1 | 2 | 3 | 4 |
|---|---|---|---|---|
| Conditions | | | | |
| Preprocess-1 (wet treatment) | Dilute hydrofluoric acid treatment, pure rinsing, and spin drying | Dilute hydrofluoric acid treatment, pure rinsing, and spin drying | Dilute hydrofluoric acid treatment, pure rinsing, and spin drying | Dilute hydrofluoric acid treatment, pure rinsing, and spin drying |
| Preprocess-2 ($H_2$ baking) | 900° C., 10 min | 900° C., 10 min | 900° C., 10 min | 900° C., 10 min |
| Film forming temp. (° C.) | 725° C. | 725° C. | 750° C. | 650° C. |
| Pressure during film formation (Pa) | $7.80 \times 10^{-2}$ | $6.90 \times 10^{-2}$ | $7.50 \times 10^{-2}$ | $8.20 \times 10^{-2}$ |
| Water plus oxygen partial pressure during film formation (Pa) | About $1 \times 10^{-4}$ to $5 \times 10^{-4}$ | About $1 \times 10^{-4}$ to $5 \times 10^{-4}$ | About $5 \times 10^{-8}$ | About $5 \times 10^{-8}$ |

As shown in Table 1, the water plus oxygen partial pressure is highest for sample-1 and lower for sample-3 and 4. First, to evaluate differences in surface roughness among the samples in a simplified manner, the samples were visually observed in a darkroom by using a light-gathering lamp. A result was as follows:

sample-1>sample-2>sample-3=sample-4.

The visual inspection also confirmed that the degree of surface roughness is higher when the water plus oxygen partial pressure is higher.

silicon epitaxial growth (see FIG. 2). In the measurements with the atomic force microscope (AFM), the measurement object size was set at about 2 μm×2 μm.

TABLE 2

| Sample No. | Ultraviolet spectral reflectance (%) | AFM measurement values | | Thickness of epitaxial growth layer (nm) | Concentration of oxygen in epitaxial growth layer by (SIMS) | |
|---|---|---|---|---|---|---|
| | | RMS (nm) | Rmax (nm) | | O-peak concentration (atoms/cm$^3$) | O-peak depth (nm) |
| 1 | 61.03 | 9.00 | 83.0 | 193.0 | 2.00 × 10$^{20}$ | 175 |
| 2 | 77.68 | 4.50 | 48.0 | 271.7 | 5.00 × 10$^{19}$ | 220 |
| 3 | 87.49 | 0.24 | 2.4 | 206.9 | Lower than detection limit | — |
| 4 | 87.43 | 0.21 | 2.0 | 277.2 | Lower than detection limit | — |

Then, the samples were subjected to a measurement of ultraviolet reflectance in which ultraviolet light in a wavelength range of 200–400 nm was applied to a measurement object approximately vertically (about 90°) and the ultraviolet spectrophotometer shown in FIG. 4 was used which is capable of measurement in a wavelength range of 190–900 nm.

Figure 17:
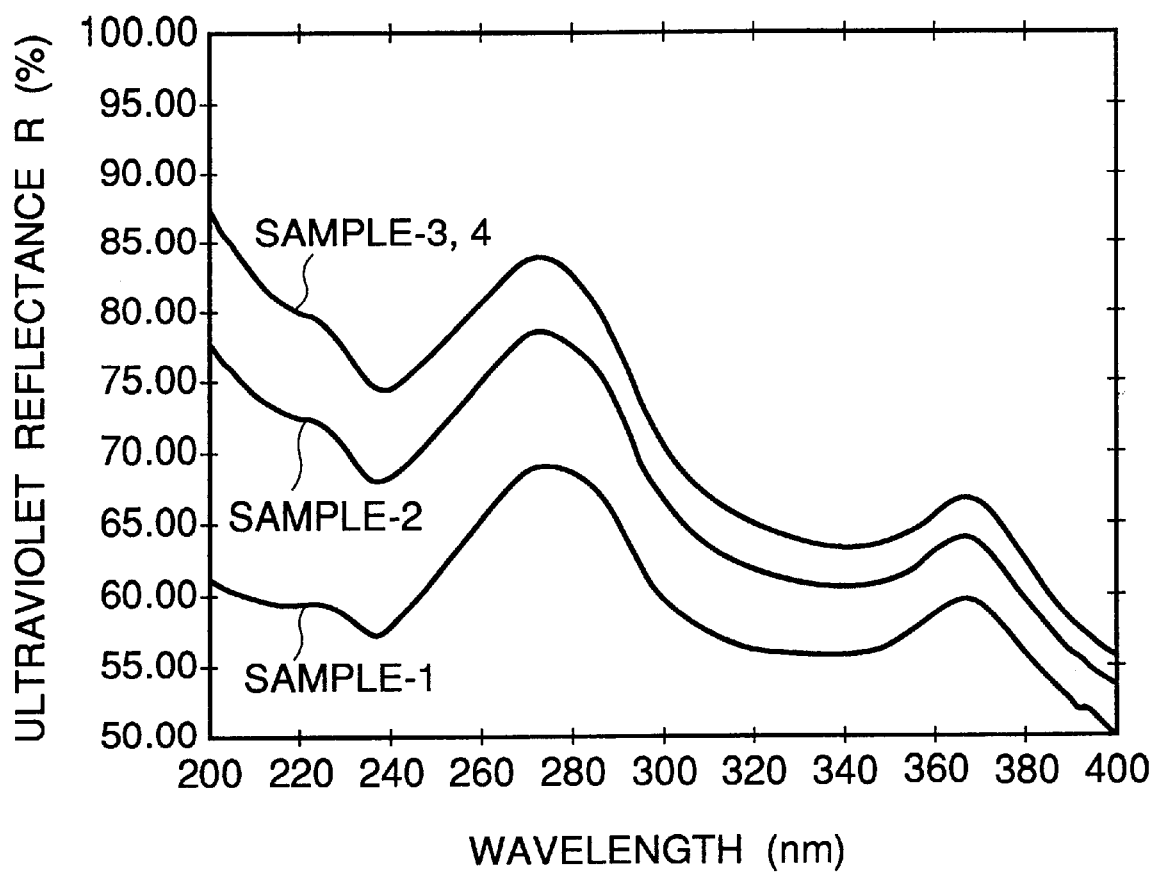
FIG. 17 shows ultraviolet reflectance spectra of samples in an Example of the invention.

FIG. 17 shows measured reflectance spectra. The measurement time was about 5 minutes per sample. Since the samples of this experiment were single crystal silicon epitaxial growth layers, the spectra have peaks at about 280 nm and have similar tendencies as the above-described single crystal spectrum shown in FIG. 3.

Attention should be paid to the ultraviolet reflectance values at a wavelength of 200 nm, which well correspond to the degrees of surface roughness of the respective samples in the above-described visual inspection. That is, a sample having a higher degree of surface roughness is lower in ultraviolet reflectance. This is in good agreement with Equation (1), that is, R exp(–4πσλ).

Further, a surface roughness measurement was performed on sample-1 to 4 by using the atomic force microscope. Measurement results are shown in Table 2. As shown in FIGS. 8A and 8B, measurement values were plotted to determine a correlation between the surface roughness and the above-described ultraviolet reflectance at a wavelength of 200 nm. In the surface roughness measurement using the atomic force microscope, the root-mean-square roughness (RMS) and the maximum height (peak-to-valley value; Rmax (range maximum)) were determined.

As seen from FIG. 8, it was found that measurement values of the ultraviolet specular reflectance R at 200 nm and those of RMS and Rmax obtained by using the atomic force microscope of silicon epitaxial growth layers formed on silicon substrates have first-order inversely proportional relationships that are represented by the following correlation formulae (A'):

$$RMS = -0.33361 \times R + 29.645 \ (nm)$$

$$Rmax = -3.0819 \times R + 275.49 \ (nm) \quad (A')$$

By using these correlation formulae, RMS and Rmax of another sample can be determined (quantified) by a calculation without the need for using the atomic force microscope if the ultraviolet reflectance R at 200 nm is measured.

Table 2 also shows evaluation results of the oxygen concentration by secondary ion mass spectrometry (SIMS), which confirm that the surface roughness of the samples depends on the water/oxygen partial pressure during the As seen from Table 2, an oxygen concentration peak was detected at the interface between the silicon substrate and the silicon epitaxial growth layer in each of sample-1 and 2 that are high in the degree of surface roughness. The surface of the silicon epitaxial layer of sample-1 was etched with a silicon selective etching liquid (a mixed liquid of hydrofluoric acid, nitric acid, acetic acid, and pure water) and was observed to check stacking faults. As a result, a fault density of 4×10$^6$ cm$^{-2}$ was obtained, which is not suitable for practical use.

As is apparent from this Example, the inventors have first confirmed experimentally that a relationship similar to Equation (1) holds for a silicon epitaxial growth layer formed on a silicon substrate. It has also been verified experimentally that there is a correlation between a measurement value of the ultraviolet reflectance R and measurement values of the surface roughness obtained by using an atomic force microscope (AFM). It has also been found that the physical mechanism relating to this correlation is represented by stacking faults that are caused by mixing of oxygen during growth of an epitaxial layer.

The invention is not limited to the above-described embodiments and Example and various modifications can be made based on its technical concept.

For example, the conditions of and the means for the surface roughness and reflectance measurements of an epitaxial growth layer can be selected properly from known ones. The wavelength of ultraviolet light for measurement may be set in a range of 190–210 nm as long as a measured reflectance value correlates with surface roughness values measured by an atomic force microscope.

In addition to a base layer as an epitaxial growth layer, the invention can similarly be applied to an epitaxial wafer for MOSFETs and an epitaxial growth layer of source and drain portions formed by selective epitaxial growth.

As described above, according to the invention, to evaluate the surface roughness of an epitaxial growth layer formed on a substrate, the reflectance of epitaxial growth layers is measured by applying shorter-wavelength ultraviolet light to the surfaces of the respective epitaxial growth layers, and a correlation between measurement values of the reflectance and the surface roughness of the epitaxial growth layers is determined. Therefore, the surface roughness of the epitaxial growth layer can be measured and evaluated simply and conveniently. For example, the reflectance and the surface roughness of epitaxial growth layers formed on samples may be measured and a correlation between two kinds of measurement values may be determined in advance. In this case, the surface roughness of an epitaxial growth layer as an ensuing measurement object can be determined by measuring only its reflectance and calculating predetermined correlation formulae using a measured reflectance value.

As a result, the loss of time that would otherwise occur in measuring the surface roughness in development or manufacture of an epitaxial growth layer can be eliminated, and the degree of oxygen mixing (i.e., the crystal defect concentration) that obstructs the epitaxial growth can be known easily. Further, by feeding back an evaluation result to a manufacturing process of an epitaxial growth layer, the productivity can be increased through improvement of the manufacturing process or the conditions for forming the epitaxial growth layer and manufacture of high-quality products is enabled.

[Table 1]
Sample No.
Conditions

Preprocess-1 (wet treatment)
Dilute hydrofluoric acid treatment, pure rinsing, and spin drying Preprocess-2 ($H_2$ baking)
900° C., 10 min
. . .
Film forming temperature Pressure during film formation Water plus oxygen partial pressure during film formation
About $1\times10^{-4}$ to $5\times10^{-4}$
. . .
[Table 2]
Sample No.

Ultraviolet spectral reflectance

AFM measurement values

Thickness of epitaxial growth layer

Concentration of oxygen in epitaxial growth layer (by SIMS)
0 peak concentration (atoms/cm$^3$)
Lower than detection limit
0-peak depth (nm)

What is claimed is:

1. A method for evaluating surface roughness of an epitaxial growth layer formed on a substrate, comprising the steps of:
   (a) measuring reflectance of epitaxial growth layers by applying ultraviolet light to surfaces of the respective epitaxial growth layers;
   (b) determining a correlation between measurement values of the reflectance and surface roughness of the epitaxial growth layers; and
   (c) wherein the ultraviolet light has a single wavelength between 190 and 210 nm.

2. The method according to claim 1, wherein specular reflectance of the epitaxial growth layers is measured by using an ultraviolet spectrophotometer with an incident angle of the ultraviolet light with respect to the surfaces of the respective epitaxial growth layers set at about 90°.

3. The method according to claim 1, comprising the steps of:
   measuring surface roughness of first epitaxial growth layers by using an atomic force microscope; and
   determining a correlation between measurement values of the surface roughness and measurement values of ultraviolet specular reflectance of the first epitaxial growth layers.

4. The method according to claim 3, comprising the step of quantifying surface roughness of a second epitaxial growth layer by applying a measurement value of ultraviolet specular reflectance of the second epitaxial growth layer to the correlation.

5. The method according to claim 4, comprising the steps of:
   determining a correlation formula of the correlation; and
   determining the surface roughness of the second epitaxial growth layer by substituting the measurement value of the specular reflectance into the correlation formula.

6. The method according to claim 3, wherein the substrate is a silicon substrate and the epitaxial growth layer is a silicon epitaxial growth layer, and wherein correlations between measurement values of root-mean-square roughness RMS and a maximum height Rmax of surfaces of the first epitaxial growth layers obtained by using the atomic force microscope and the measurement values of the ultraviolet specular reflectance R of the first epitaxial growth layers are formulated as correlation formulae.

$$RMS = -a \times R + b$$

$$Rmax = -c \times R + d$$

where a, b, c, and d are constants.

7. A method of measuring reflectance of an epitaxial growth layer formed on a substrate to evaluate surface roughness of the epitaxial growth layer, comprising the step of specular reflectance of the epitaxial growth layer with an ultraviolet spectrophotometer by applying ultraviolet light, the ultraviolet light having a single wavelength between 190 and 210 nm, to a surface of the epitaxial growth layer at an incident angle of about 90°.

8. The method according to claim 7, wherein the substrate is a silicon substrate.

9. A manufacturing method of a semiconductor device comprising the step of forming an epitaxial growth layer on a semiconductor substrate, further comprising the steps of:
   (a) measuring reflectance of epitaxial growth layers by applying ultraviolet light to surfaces of the respective epitaxial growth layers;
   (b) determining a correlation between measurement values of the reflectance and surface roughness of the epitaxial growth layers; and
   (c) wherein the ultraviolet light has a single wavelength between 210 and 290 nm.

10. The manufacturing method according to claim 9, further comprising the steps of:
    evaluating surface roughness of an epitaxial growth layer based on the correlation; and
    controlling conditions for forming an ensuing epitaxial growth layer based on an evaluation result of the surface roughness.

11. The manufacturing method according to claim 9, wherein the semiconductor substrate is a silicon substrate, the epitaxial growth layer is a silicon epitaxial growth layer as a base layer, and the semiconductor device is a vertical bipolar transistor.

12. The manufacturing method according to claim 9, wherein specular reflectance of the epitaxial growth layers is measured by using an ultraviolet spectrophotometer with an incident angle of the ultraviolet light with respect to the surfaces of the respective epitaxial growth layers set at about 90°.

13. The manufacturing method according to claim 9, comprising the steps of:

measuring surface roughness of first epitaxial growth layers by using an atomic force microscope; and determining a correlation between measurement values of the surface roughness and measurement values of ultraviolet specular reflectance of the first epitaxial growth layers.

14. The manufacturing method according to claim 13, comprising the step of quantifying surface roughness of a second epitaxial growth layer by applying a measurement value of ultraviolet specular reflectance of the second epitaxial growth layer to the correlation.

15. The manufacturing method according to claim 14, comprising the steps of:

determining a correlation formula of the correlation; and determining the surface roughness of the second epitaxial growth layer by substituting the measurement value of the specular reflectance into the correlation formula.

16. The manufacturing method according to claim 13, wherein the substrate is a silicon substrate and the epitaxial growth layer is a silicon epitaxial growth layer, and wherein correlations between measurement values of root-mean-square roughness RMS and a maximum height Rmax of surfaces of the first epitaxial growth layers obtained by using the atomic force microscope and the measurement values of the ultraviolet specular reflectance R of the first epitaxial growth layers are formulated as correlation formulae.

$$RMS = -a \times R + b$$

$$R\max = -c \times R + d$$

where a, b, c, and d are constants.

* * * * *